US005487933A

United States Patent [19]
White

[11] Patent Number: 5,487,933
[45] Date of Patent: Jan. 30, 1996

[54] PROSTHETIC ARTICLES AND METHODS FOR PRODUCING SAME

[75] Inventor: Eugene W. White, Rossiter, Pa.

[73] Assignee: Interpore International, Irvine, Calif.

[21] Appl. No.: 308,762

[22] Filed: Sep. 19, 1994

Related U.S. Application Data

[60] Continuation-in-part of Ser. No. 134,260, Oct. 8, 1993, which is a division of Ser. No. 647,999, Jan. 30, 1991, Pat. No. 5,348,788.

[51] Int. Cl.$^6$ .................... B32B 3/24; A61F 2/28
[52] U.S. Cl. .......... 428/131; 428/134; 428/156; 428/220; 428/213; 428/338; 623/11; 623/16; 264/220; 264/227; 264/310
[58] Field of Search ............ 428/131, 134, 428/156, 220, 213, 338; 623/11, 16; 264/220, 227, 310

[56] References Cited

U.S. PATENT DOCUMENTS

| | | | |
|---|---|---|---|
| 3,852,832 | 12/1974 | McGhan et al. | 3/36 |
| 4,673,409 | 6/1987 | Van Kampen | 623/23 |
| 4,839,215 | 6/1989 | Starling et al. | 428/131 |
| 4,865,603 | 9/1989 | Noiles | 623/18 |
| 4,978,355 | 12/1990 | Frey et al. | 623/16 |
| 5,011,494 | 4/1991 | von Recum et al. | 623/11 |
| 5,030,233 | 7/1991 | Ducheyne | 623/16 |
| 5,053,264 | 10/1991 | Beretta | 428/131 |
| 5,147,402 | 9/1992 | Bohler et al. | 623/16 |
| 5,192,324 | 3/1993 | Kenna | 623/16 |
| 5,222,987 | 6/1993 | Jones | 623/66 |
| 5,282,861 | 2/1994 | Kaplan | 623/16 |
| 5,342,919 | 8/1994 | Dickens, Jr. | 528/323 |

Primary Examiner—William P. Watkins, III
Attorney, Agent, or Firm—Hopgood, Calimafde, Kalil & Judlowe

[57] ABSTRACT

A porous mesh structure is prepared in sheet form having a unique arrangement of main and secondary troughs on a first surface, and openings extending therethrough. The arrangement of troughs and openings creates an elaborate matrix of pores when the sheet is layer on itself in a front to back manner. This arrangement of pores and support structure emulates certain cortical bone structures and is therefore very effective as an artificial bone material. In addition, the porous structure has significant other potential uses outside the medical field and can be effectively applied accordingly, based on its fundamental structural attributes.

17 Claims, 2 Drawing Sheets

PROSTHETIC ARTICLES AND METHODS FOR PRODUCING SAME

RELATED APPLICATIONS

This is a continuation-in-part of U.S. patent application Ser. No. 08/134,260 filed Oct. 8, 1993, which is a divisional of U.S. patent application Ser. No. 07/647,999 filed Jan. 30, 1991 (now U.S. Pat. No. 5,348,788).

FIELD OF THE INVENTION

The present invention generally relates to materials which simulate human tissue for use as prosthesis. More particularly, the invention is directed to novel three-dimensional structures made from select materials and processes for producing the three-dimensional structures from the select materials.

BACKGROUND OF THE INVENTION

Prosthetic materials are engineered elements which can achieve biological function when placed within a living organism. An important class of prosthetic materials are those which are used to repair and replace human body tissue such as osseous matter. To replace biological tissue in an acceptable, long lasting manner, the replacement materials must join with the surrounding living matter. Proper melding is achieved through the use of an appropriate material having a micro-network of capillaries permeating the structure to permit living tissue in-growth.

Such porous networks must be continuous, permitting unrestricted passage of blood and other body fluids from the surrounding tissue while also providing structural support. This can be easily envisioned in the design of artificial bone wherein osseous replacement materials must support the forces and stresses associated with the skeletal system and simultaneously allow passage of blood gases, nutrients, waste products and other extracellular material to and from the surrounding tissue.

In reconstructive surgery such as repair of highly comminuted fractures, healing can be accelerated by inclusion of materials having such porous matrix adjacent the break point to enhance bone growth. Rebuilding of damaged long bones can also benefit from insertion of such porous prosthetic materials to re-achieve the desired pre-damage shape and strength.

Such porous yet semi-rigid materials are found in nature. For example, spiny starfish, certain sea urchins and coral exhibit a solid structure formed of calcium carbonate having a network of interconnecting pores and significant void volume in the form of a micro-porous matrix. Specifically, the slate pencil sea urchin has cigar-shaped protrusions that have a void volume of 50 percent and a porous structure with pore diameters of approximately 25 µm. Certain coral provide similar attributes with pore diameters of approximately 250–600 µm.

In the past, these aquatic materials were used to form biologically acceptable structures such as through hydrothermal treatment of the calcium carbonate skeletons to form hydroxyapatite. More detailed discussion of such techniques may be found in U.S. Pat. Nos. 3,890,107, 3,929,971, 4,231,979, 4,722,870 and 4,861,733, the teachings of which are incorporated by reference herein.

Although these procedures offer a unique class of structures, they are accompanied by several significant drawbacks. The naturally forming aquatic structures are never completely uniform and often exhibit imperfections detrimental to surgical implantation. In addition, the materials are expensive to harvest, and such gleaning of nature has raised environmental impact concerns in some quarters.

These problems have led to a search for techniques to engineer and manufacture porous materials having specifically delineated structural properties in a controlled manner. In this search, applicant has developed a unique collection of porous articles of the type discussed above. These are disclosed in U.S. patent application Ser. No. 07/647,999 (filed Jan. 30, 1991) (U.S. Pat. No. 5,348,788) identified above, the contents of which is incorporated by reference herein as if restated in full.

Related thereto, applicant has developed several important advancements which are described herein below.

OBJECTS AND SUMMARY OF THE PRESENT INVENTION

It is an object of the present invention to provide materials which simulate human tissue for use in repair and replacement of osseous matter in the form of porous materials that have a three-dimensional network of interconnecting pores.

Another object of the present invention is to provide materials which simulate human osseous tissue for use as prosthesis in the form of porous materials that have a three-dimensional network of interconnecting pores and a void volume percent between 20 and 80.

It is another object of the present invention to provide a porous article with a substantially anisotropic distribution of pores wherein the pore diameter ranges between 25 and 2500 µm.

It is a further object of the present invention to provide biologically compatible, curable, bone-like compositions and three-dimensional structures made therefrom.

It is yet another object of the invention to provide biologically compatible hydroxyapatite, hydroxyapatite/collagen and hydroxyapatite/gelatin compositions and three-dimensional structures made therefrom.

It is a further object of the present invention to provide a bone substitute material which when properly configured simulates osteon evacuated cortical bone.

It is another object of the present invention to provide a method for manufacturing biologically compatible, curable, bone-like compositions and three-dimensional structures made from such compositions for use as cement in bone repair or as bone-substitute materials.

It is also another object of the invention to provide a method for making hydroxyapatite compositions, hydroxyapatite/collagen and hydroxyapatite/gelatin compositions and three-dimensional structures made from such compositions for use as cement in bone repair or as bone-substitute materials as tailored to specific system constraints.

It is yet another object of the present invention to provide methods for making porous structures that have varying industrial applications such as heat exchangers, spargers, catalytic support matrices and filter media.

The above and other objects of the present invention are realized in illustrative compositions suitable for use in repair of damaged bone and bone-simulating material comprising biologically compatible, curable, bone-like compositions such as hydroxyapatite, hydroxyapatite/collagen, hydroxyapatite/gelatin, and other bio-materials such as polyfunctional carboxylic acid substrates described in U.S. Pat. No. 4,218,255, calcium phosphate slurries and pastes described in U.S.

Patent No. 4,612,053, non-bioresorbable calcium phosphate described in U.S. Pat. No. 4,619,655, polymer based calcium phosphates described in U.S. Pat. No. 4,843,112, carbonated hydroxyapatite such as described in U.S. Pat. No. 4,880,610, organic acid-calcium phosphates described in U.S. Pat. No. 4,902,649, acidic phosphates described in U.S. Pat. No. 5,053,212, acidic citrates described in U.S. Pat. No. 5,149,368, polysaccharide calcium phosphates described in U.S. Pat. No. 5,180,426, calcium alkali-polyfunctional carboxylic acid substrates described in U.S. Pat. No. 5,218,035, calcium alkali-acidic citrates described in U.S. Pat. No. 5,262,166, calcium salts-polyfunctional acid substrates described in U.S. Pat. No. 5,281,265, and tannin/collagen-calcium phosphates described in WIPO Patent Publication Nos. WO 90/00892 and WO 90/01341, the teachings of which are herein incorporated by reference.

A discussion of some of these materials may also be found in Stupp et al., *Organoapatites: Materials for Artificial Bone*, J. Biomedical Materials Res., Vol. 27, pages 301–311 (1993), the teachings of which is incorporated by reference herein.

Hydroxyapatite has a nominal composition of $Ca_{10}(PO_4)_6(OH)_2$ and comprises the principal mineral in human bones. The metal mold used in the forming process is machined by various surface shaping techniques that are known, such as computer guided milling, photolithography and electron discharge machining. Suitable mold metals include steel and brass and other rigid substrate materials well known to those skilled in the art.

A porous mesh suitable for emulating cortical bone structure can be made as follows. The mesh attributes are first formed in a master that is machined from metal sheets in a predetermined, scaled pattern on a specifically delineated surface area. From the metal masters are produced, by replication, as many "negative working masters" as desired.

The negative masters are made of silicone rubber or other suitable substitute materials evident to one skilled in these arts. With a light coating of mold release agent, whole sheets of replicas are retrieved. Silicone rubber is ideal for some applications but other applications may require more rigid materials. The silicone negative master is the inverted replica of the original metal master.

Bone substitute materials are subsequently produced from the silicone negative masters. Preferably, a mixture containing specific and predetermined amounts of water, gelatin and calcium phosphate are prepared at a set temperature. Bovine gelatin ($C_{76}H_{124}O_{29}N_{24}S_x$) can be used but any albumin usually obtained from boiling animal bones and cartilage under pressure with water are suitable. Collagen may also be added as an alternate or additional reagent. Collagen of the type contemplated herein includes a hydroxyproline, glycine-type protein which is the chief organic constituent of connective tissue and bones, which yields gelatin when steam autoclaved in water, and which is usually comprised of 50.75% carbon, 6.47% hydrogen and 17.86% nitrogen.

The preferred mixture is applied hot with a suitable spatula to a selected silicone negative master and worked into the formed pattern. The assembly is then chilled for a predetermined time period allowing the gelatin to set. The gelled mix is released from the master and wrapped on a suitably shaped mandril. The shape of the selected mandril closely corresponds to the shape of the actual bone in the desired repair site. After the suitable shape is achieved, the hydroxyapatite material is slipped off the mandril and allowed to dry.

The resulting shaped material must then be stabilized before use in the human body. Hydroxyapatite can be stabilized by known techniques such as thermal/vacuum processing or chemical cross-linking. Gelatin cross-link treatment renders the gelatin within the hydroxyapatite/gelatin composite less biodegradable. Alternatively, the final process stage can be a high temperature burn off of the gelatin binder to sinter the hydroxyapatite body for strength. If such a burn off is contemplated, the starting materials should have a higher loading of calcium phosphate relative to the gelatin.

The foregoing features of the present invention may be more fully appreciated by reference to the following detailed description of the specific embodiments thereof, in conjunction with the associated figures.

DETAILED DESCRIPTION OF THE PRESENT INVENTION

The present invention is directed to the preparation of a new man made structure comprised of materials suitable for use in repair of damaged bone and bone-simulating material comprising biologically compatible, curable, bone-like compositions such as hydroxyapatite, hydroxyapatite/collagen, hydroxyapatite/gelatin, and other bio-materials such as described in the above-noted patents.

The new sheet structure is specifically designed for assembly into a variety of shapes, not just rectangular blocks, that more closely correspond to the shapes of the actual bone in many repair sites such as hollow cylindrical or doubly curved plate shapes. The porous mesh sheets provide the basis for a three-dimensional structure that closely emulates the anisotropic network associated with cortical bone mass.

Figure 1:
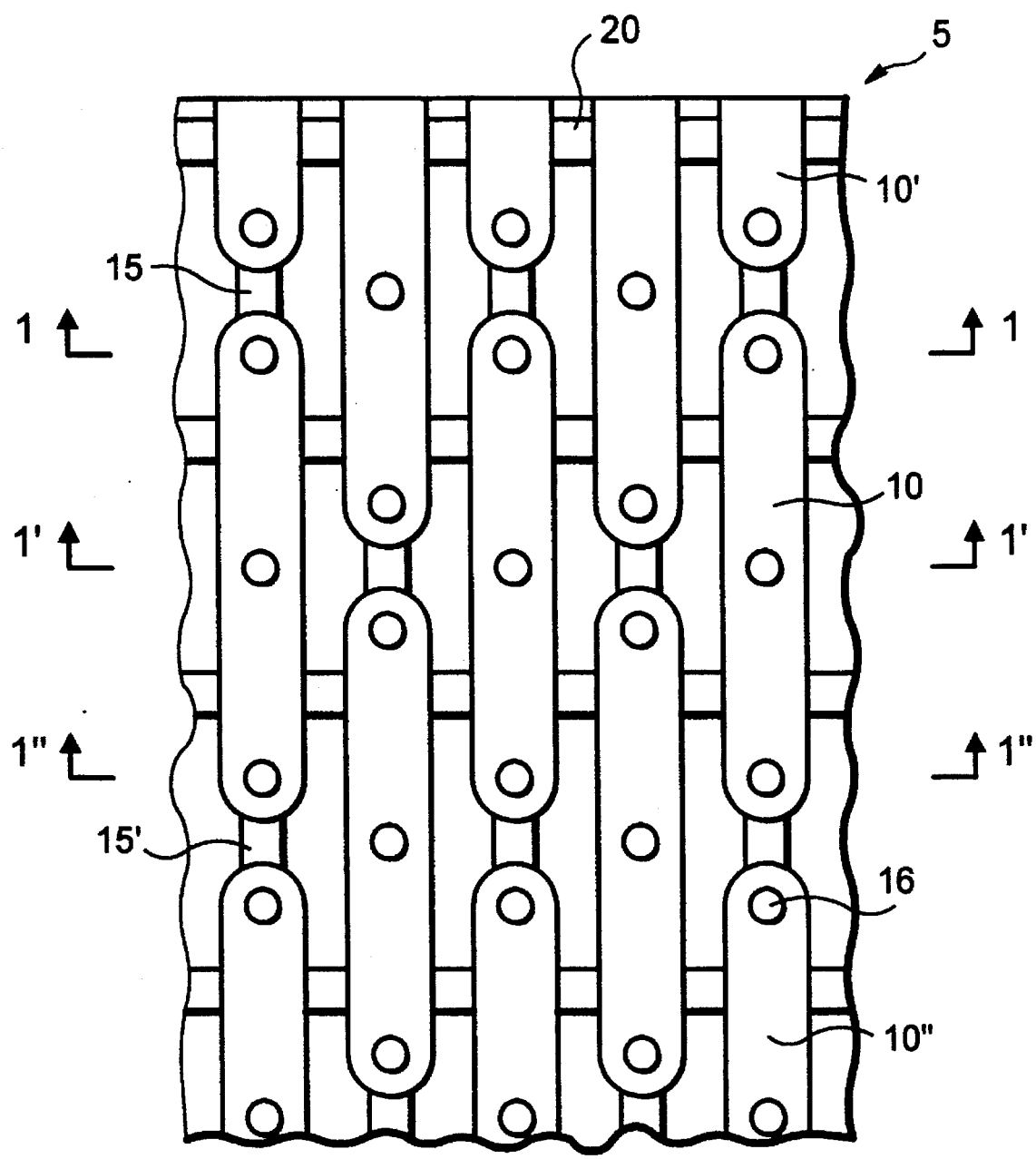
FIG. 1 depicts a plan view of the preferred sheet structure of the present invention.

FIG. 1 depicts the preferred sheet structure of the preset invention shown in scale at from 100 to 1000 μm per division (squares in the figure). Two masters were machined to this sketch using a scale of 0.015 inches per division (375 μm). The masters were machined in 2.65×9 inch brass sheets with the pattern machined on an area of two by eight inches.

The brass masters are used to produce, by replication, as many "negative working masters" as desired. FIG. 1 shows a continuous sheet generally designated with the numeral 5 having a series of substantially parallel and linked main troughs 10 extending in one horizontal direction along the sheet, with each main trough 10 further linked to co-linear troughs 10' and 10" by a series of secondary shallow troughs 15 and 15'.

Each main trough (exemplified by trough 10) has one or more small openings 16 extending through the bottom of each main trough. Openings 16 have a diameter that is approximately ⅓ the width of main trough 10. FIG. 1 also shows a second series of secondary shallow troughs 20 extending perpendicular to and connecting the main troughs such as 10.

Figure 2B:
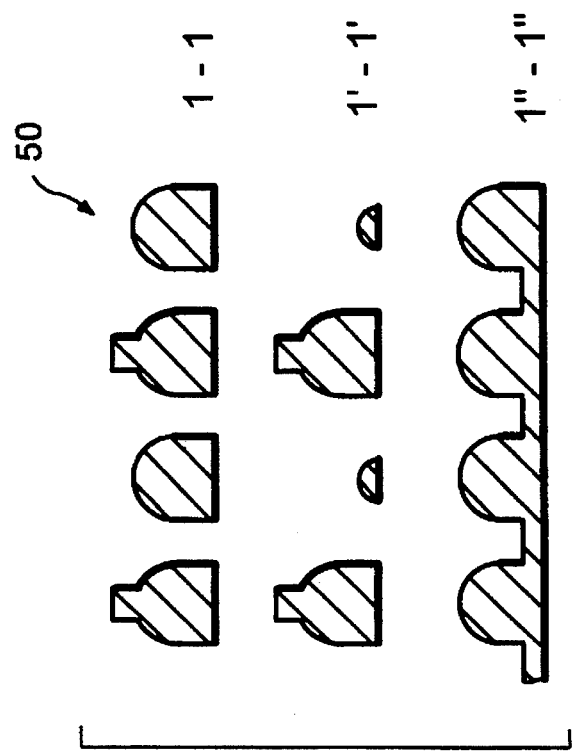
FIG. 2B provides a negative cross-sectional view of the sheet of FIG. 1, taken at planes 1—1, 1'—1' and 1"—1".
Figure 2A:
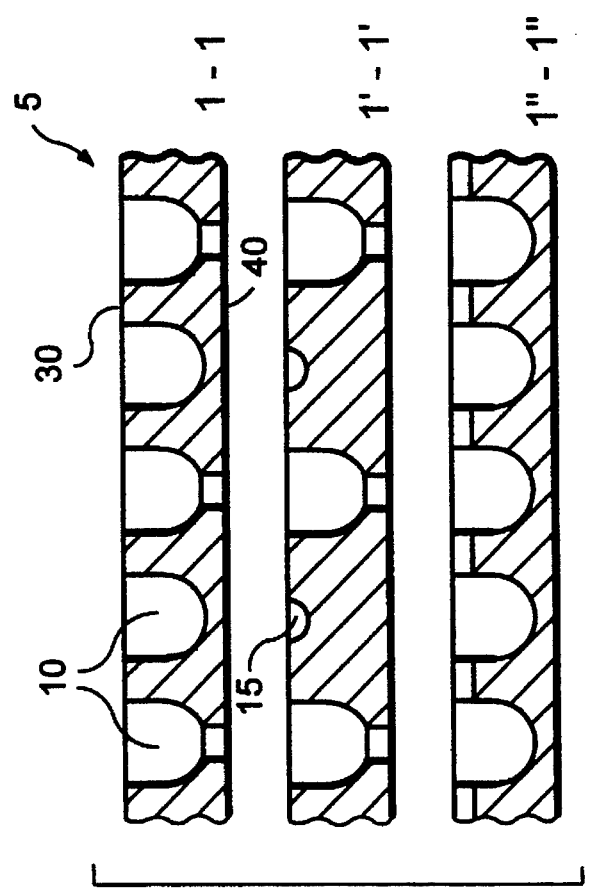
FIG. 2A provides a positive cross-sectional view of the sheet of FIG. 1, taken at planes 1—1, 1'—1' and 1"—1".

FIG. 2A provides a positive cross-sectional view of the sheet of FIG. 1, taken at planes 1—1, 1'—1' and 1"—1". Shee 5 is shown as being a continuous sheet having a substantially uniform thickness between opposing sides 30 and 40. A series of substantially parallel and linked main troughs 10 extend in one horizontal direction along a first side 30 of sheet 5. Main troughs 10 have a depth in sheet 5 that extends substantially into the sheet with each main trough 10 spaced from adjacent main troughs by a distance approximately ½ a width of the main trough. Linking series of secondary shallow troughs 15 are also shown.

One or more small openings 16 are shown in FIG. 2A extending through the bottom of each main trough 10 into second side 40 of sheet 5. Openings 16 have a diameter that is approximately ⅓ the width of main trough 10.

FIG. 2B provides a negative cross-sectional view of the sheet of FIG. 1, taken at planes 1—1, 1'—1' and 1"—1". Negative masters such as 50 shown in FIG. 2B can be made in silicone rubber. With only a light coating of mold release agent, whole sheet replicas are made with excellent fidelity. Silicone rubber is ideal for some applications but other applications may require more rigid materials.

Bone substitute material are made from the silicone negative masters such as depicted in FIG. 2B. For this a mixture containing 50 parts water, 25 parts bovine gelatin and 10 parts tricalcium phosphate was used. The mixture was prepared at 80° C. The mix was applied hot with a Teflon spatula to the silicone master and worked into the structure. While still hot, the mix was manipulated such that it was uniformally in the structure and excess material was easily worked aside exposing the top surfaces of the protruding silicone structure.

Once in the silicone mold, the assembly was chilled in the refrigerator for about 10 minutes. This allowed the gelatin to set giving it good handling strength. The gelled mix easily completely released from the mold and was trimmed with scissors and wrapped on a wax paper covered mandril (glass test tube). Just prior to wrapping on the mandril, the one surface of the sheet was misted with water to produce the layer-to-layer gluing effect. The now cylinder shaped assembly was slipped off the mandril, was paper removed from inside the hollow cylinder and the part was allowed to dry in air overnight. It is important to remove the mandril otherwise drydown shrinkage will produce cracks in the part and linear shrinkage will be distorted. As discussed above, the resulting part must be stabilized prior to use in body.

The above-described arrangement is merely illustrative of the principles of the present invention. Numerous modifications and adaptations thereof will be readily apparent to those skilled in the art without departing from the spirit and scope of the present invention.

What is claimed is:

1. A non-woven porous mesh in sheet form, said mesh comprising:

a continuous sheet having a substantially uniform thickness between opposing sides;

a series of substantially parallel and linked main troughs extending in one horizontal direction along a first side of said sheet, said main troughs having a depth in said sheet that extends substantially into said sheet, said main troughs are spaced from adjacent main troughs by a distance approximately ½ a width of said main trough, said main troughs further linked to co-linear troughs by a first series of secondary shallow troughs;

one or more small openings extending through the bottom of each main trough to a second side of said sheet, said openings having a diameter that is approximately ⅓ the width of said main trough; and a second series of secondary shallow troughs extending substantially perpendicular to and connecting said main troughs.

2. The porous mesh of claim 2 wherein said sheet thickness ranges between 200 to 2000 microns.

3. The porous mesh of claim 2 wherein the depth of said secondary troughs are approximately ½ the depth of said main troughs.

4. The porous mesh of claim 2 wherein said main troughs extend approximately 80 percent through said sheet thickness.

5. The porous mesh of claim 1 wherein said small openings have a diameter that is approximately equal to the width of said secondary troughs.

6. The porous mesh of claim 5 wherein said first series of secondary troughs extend substantially in parallel through said sheet.

7. The porous mesh of claim 6 wherein said second series of secondary troughs extend substantially parallel through said sheet.

8. A porous three dimensional body formed by wrapping the porous mesh of claim 1 around a mandrel having a select shape characteristic, wherein said porous mesh is wrapped in multiple layers to form a network of three dimensional pores extending throughout said body, and said mesh is layered front-to-back.

9. The porous body of claim 8 wherein said shape characteristic is cylindrical.

10. The porous body of claim 8 wherein said layers of mesh are adhesive bonded to adjacent layers.

11. A method of forming a porous sheet of claim 1 comprising the steps of:

making a primary form corresponding in shape to the final mesh structure;

casting a negative form by placing a curable material in fluid state into said primary form, allowing said material to cure and removing said cured negative form from said primary form;

casting said porous mesh by placing a mesh material in said negative form and allowing said mesh material to partial cure;

before said mesh material is completely cured, remove said mesh material from said negative form and wrap it around a shape defining mandrel; and complete mesh curing while on said shape defining mandrel to form a shaped body having a three dimensional pore structure.

12. The method of claim 11 wherein said primary form is made by machining a metal sheet.

13. The method of claim 12 wherein said metal sheet is brass.

14. The method of claim 12 wherein said curable material is silicone rubber.

15. The method of claim 11 wherein said curable mesh material is hydroxyapatite (HA) and gelatin.

16. The method of claim 15 further comprising the step of chilling the HA prior to wrapping the mesh around said mandrel.

17. The method of claim 16 further comprising the step of drying the shaped body after removing it from the mandrel.

* * * * *